(12) United States Patent
Liu et al.

(10) Patent No.: US 11,443,834 B2
(45) Date of Patent: Sep. 13, 2022

(54) AUTOMATIC CONFORMATION ANALYSIS METHOD FOR QUASI-DRUG ORGANIC MOLECULES

(71) Applicant: SHENZHEN JINGTAI TECHNOLOGY CO., LTD., Guangdong (CN)

(72) Inventors: Yang Liu, Guangdong (CN); Peiyu Zhang, Guangdong (CN); Mingjun Yang, Guangdong (CN); Guangxu Sun, Guangdong (CN); Jian Ma, Guangdong (CN); Lipeng Lai, Guangdong (CN); Shuhao Wen, Guangdong (CN)

(73) Assignee: SHENZHEN JINGTAI TECHNOLOGY CO., LTD., Guangdong (CN)

( * ) Notice: Subject to any disclaimer, the term of this patent is extended or adjusted under 35 U.S.C. 154(b) by 770 days.

(21) Appl. No.: 16/466,645

(22) PCT Filed: May 9, 2018

(86) PCT No.: PCT/CN2018/086195
§ 371 (c)(1),
(2) Date: Jun. 5, 2019

(87) PCT Pub. No.: WO2019/134319
PCT Pub. Date: Jul. 11, 2019

(65) Prior Publication Data
US 2021/0265019 A1    Aug. 26, 2021

(51) Int. Cl.
*G16C 10/00*  (2019.01)
*G16C 20/20*  (2019.01)
*G16C 20/70*  (2019.01)

(52) U.S. Cl.
CPC ............. *G16C 10/00* (2019.02); *G16C 20/20* (2019.02); *G16C 20/70* (2019.02)

(58) Field of Classification Search
CPC ........ G16C 20/00; G16C 10/00; G16C 20/50; G06N 5/00
See application file for complete search history.

(56) References Cited

U.S. PATENT DOCUMENTS 11,119,033 B2 *   9/2021   Izumi ................... G16C 10/00
2009/0248321 A1   10/2009  Izumi et al.

FOREIGN PATENT DOCUMENTS

CN     1886659       12/2006
CN    103984878      8/2014
(Continued)

OTHER PUBLICATIONS

"International Search Report (Form PCT/ISA/210) of PCT/CN2018/086195," dated Feb. 12, 2019, pp. 1-5.

*Primary Examiner* — Lam S Nguyen
(74) *Attorney, Agent, or Firm* — JCIP Global Inc.

(57) ABSTRACT

The invention relates to an automatic conformation analysis method for quasi-drug organic molecules. The method includes: extracting a group of fragments from an input molecule, wherein there are primarily three types of fragments: a flexible bond fragment, a ring isomerism fragment and a conformation isomerism fragment; carrying out knowledge-based conformation recommendation; carrying out conformation recommendation based on force field scanning; verifying, by QM, the generated conformations, wherein if the verification succeeds, it indicates that the recommended conformations are valid; or otherwise, the force field is corrected; collecting conformation lists of the fragments; and combining and optimizing conformation parameters of the fragments through a genetic algorithm, and finding out a set of optimal conformations. The invention integrates the advantages of a knowledge-based method (Continued)

and the advantages of a computation method, so that accurate conformation recommendations can be acquired.

2 Claims, 3 Drawing Sheets

(56) References Cited

FOREIGN PATENT DOCUMENTS

| | | | |
|---|---|---|---|
| CN | 108763852 | | 11/2018 |
| JP | 2005508487 | * | 3/2005 |

* cited by examiner

AUTOMATIC CONFORMATION ANALYSIS METHOD FOR QUASI-DRUG ORGANIC MOLECULES

CROSS-REFERENCE TO RELATED APPLICATION

This application is a 371 of international application of PCT application serial no. PCT/CN2018/086195, filed on May 9, 2018. The entirety of the above-mentioned patent application is hereby incorporated by reference herein and made a part of this specification.

BACKGROUND OF THE INVENTION

1. Technical Field

The invention belongs to the field of analog computation of small quasi-drug organic molecules, and particularly relates to an automatic conformation analysis method for quasi-drug organic molecules.

2. Description of Related Art

The conformation of drug molecules has a significant influence on their bioactivity. A series of conformation changes generated under the interaction of drug molecules and receptors form a dynamic matching process, and specific pharmacological responses are given in this process. Therefore, conformation analysis and reasonable conformation generation of quasi-drug organic molecules play a crucial role in computer-aided drug design, drug crystal structure prediction, and other studies on drugs.

At present, there are two common conformation analysis or generation methods as follows.

1. Flexible bonds are scanned based on the molecular force field to create a potential energy surface and to figure out all possible extreme points.

2. Knowledge-based conformation recommendation: existing experimental conformation databases are searched for similar structure groups to provide recommended conformations.

The first method is applicable primarily to organic molecules having less than 20 flexible bonds to be searched. Particularly, one-dimensional scanning of all flexible angles is carried out by a certain strategy; then, certain flexible bonds that are able to be coupled are selected according to the steric hindrance information of the flexible angles and are then subjected to two-dimensional scanning; and finally, combination is carried out according to restricted low-energy points of the flexible angles to find out the most likely set of conformations. By adoption of this method, most of the conformational space can be efficiently traversed by means of the small-computation characteristic of the molecular force field. However, this method also has a great disadvantage that as energy computation depends mainly on the molecular force field, the computation accuracy is limited to a larger extent by the description capacity to the potential energy surface of the molecular force field. While common universal force field parameters such as GAFF and FF94 have a limited capacity to cover the chemical space of small drug molecules, and wrong conformations will be recommended if the corresponding system fails to be accurately described by the force field parameters.

The second method is suitable for conformation analysis of larger molecule structures such as carbohydrates or protein. Due to the fact that these molecules typically have a huge conformation space that cannot be traversed by scanning, conformations of these molecules can be generated only with the guidance of prior knowledge. This method is usually implemented in the following way: a target molecule is split into fragments based on a known conformation database, and then, the database is searched for identical or similar fragments; afterwards, statistical analysis is carried out on the fragments searched out to recommend the conformation of each fragment; and finally, the conformations of all the fragments are combined into an integral conformation. This method can effectively handle macromolecules, and the computation complexity linearly increases with the size increase of molecules. Because this method is based on prior knowledge, this method is suitable for handling molecules having limited groups such as carbohydrates or protein, but is not suitable for small drug molecules with high diversity and nonlinearity for the reason that fragments identical with or similar to a target fragment may fail to be searched out from the existing databases lacking effective coverage, and in this case, reasonable conformations cannot be recommended.

BRIEF SUMMARY OF THE INVENTION

To settle the above technical issue, the invention provides an automatic conformation analysis method for quasi-drug organic molecules. By adoption of the method, all reasonable conformations can be recommended by comprehensive analysis on chiral isomerism, ring isomerism, and spatial isomerism of molecules. The technical solution adopted by the invention is as follows.

The automatic conformation analysis method for quasi-drug organic molecules mainly includes the following steps.

(1) Extracting a group of fragments from an input molecule, wherein there are primarily three types of fragments: a flexible bond fragment, a ring isomerism fragment, and a conformation isomerism fragment.

The flexible bond fragment includes a flexible bond or two coupled flexible bonds, and an adjacent chemical group beside the flexible bond(s), and whether or not two flexible bonds are in a coupled relation is determined based on a topological rule; and a potential energy surface or extreme points on the flexible bond fragment are searched out by further analysis on the flexible bond fragment, so as to represent a potential energy surface of the whole molecule on this flexible bond.

The ring isomerism fragment includes a non-conjugate ring or a condensed ring consisting of a plurality of rings.

The conformation isomerism fragment includes one or more cis-trans sites or chiral centers, and a surrounding chemical environment.

(2) Carrying out knowledge-based conformation recommendation: particularly, molecular conformations including the corresponding fragments extracted in Step (1) are searched out from a pre-established conformation database, and then conformation statistics of a specific flexible bond or ring isomerism, and a specified cis-trans or chiral center selected from the molecule are carried out to obtain recommended conformations and confidence coefficients of the recommended conformations; the confidence coefficient comprise an empirical threshold, if the confidence coefficients are greater than the empirical threshold, the credibility of the knowledge-based recommendation is considered high, and the recommended conformations are directly used; or if the confidence coefficients are small, conformation analysis continues to be carried out in a more accurate way.

(3) Carrying out conformation recommendation based on force field scanning, wherein the following scanning strategies are mainly adopted: one-dimensional or two-dimensional equal-interval rotational scanning of flexible bonds, conformation scanning of flexible rings, and cis-trans or optical configuration scanning.

Based on a molecular force field, conformations generated through the scanning strategies are rapidly optimized, and energy of the conformations is calculated; then reasonable conformations are screened out according to the energy.

(4) Verifying, by quantum mechanics (QM), the conformations generated in step (3) mainly in the following two ways.

Positions of the extreme points are analyzed, and sampling computation is carried out on the extreme points as well as nearby points to determine by comparison whether or not QM is consistent with the positions of extreme points of the molecular force field.

Or, the relative energy of the recommended conformations is analyzed to verify the correlation between the QM and molecular force field computation, so that the accuracy of the force field is verified.

If the verification succeeds, it indicates that the conformations recommended in Step (3) are valid; or otherwise, it is possible that the accuracy of the force field is improper, and the force field needs to be corrected next.

(5) Correcting the force field: particularly, if a universal force field fails to accurately describe the chemical environment of the molecule, force field parameters should be improved to adapt to the molecule; upon analysis on the corresponding fragments, QM sampling computation is additionally conducted according to the flexible bond, the ring isomerism and the conformation isomerism serve as a training set for correcting the force field parameters, and then the force field parameters are corrected; the force field is scanned again after the force field parameters are corrected.

(6) Collecting conformation lists of the fragments: particularly, the conformation lists separately recommended by the fragments are collected; values expressed by the conformations (including dihedral values of the flexible bonds or isomerous space parameters of the ring isomerisms, and cis-trans or chiral identifications) are extracted to be used for subsequent parameter combination and optimization.

(7) Combining and optimizing conformation parameters of the fragments through a genetic algorithm, and finding out a set of optimal conformations through global searching.

The automatic conformation analysis method for quasi-drug organic molecules has the following technical effects.

(1) The invention integrates the advantages of a knowledge-based method and the advantages of a computation method, thereby being able to provide knowledge-based recommendations rapidly for common fragments and to provide accurate conformation recommendations for uncommon fragments by scanning computation; and computation results are stored in a knowledge database, and the knowledge-based recommendation capacity will be gradually improved with the continuous accumulation of computation.

(2) When the description capacity of a universal force field is limited, the universal force field can be corrected by QM computation to generate a special force field capable of accurately describing the fragments, so that inaccurate conformation recommendations caused by force field limitations are avoided.

(3) The conformations recommended by the fragments are combined through the genetic algorithm, so that the problem of a large space caused by direct combination of the conformations recommended by the fragments is solved.

DETAILED DESCRIPTION OF THE INVENTION

The specific technical solution of the invention is explained below in combination with embodiments.

Figure 1:
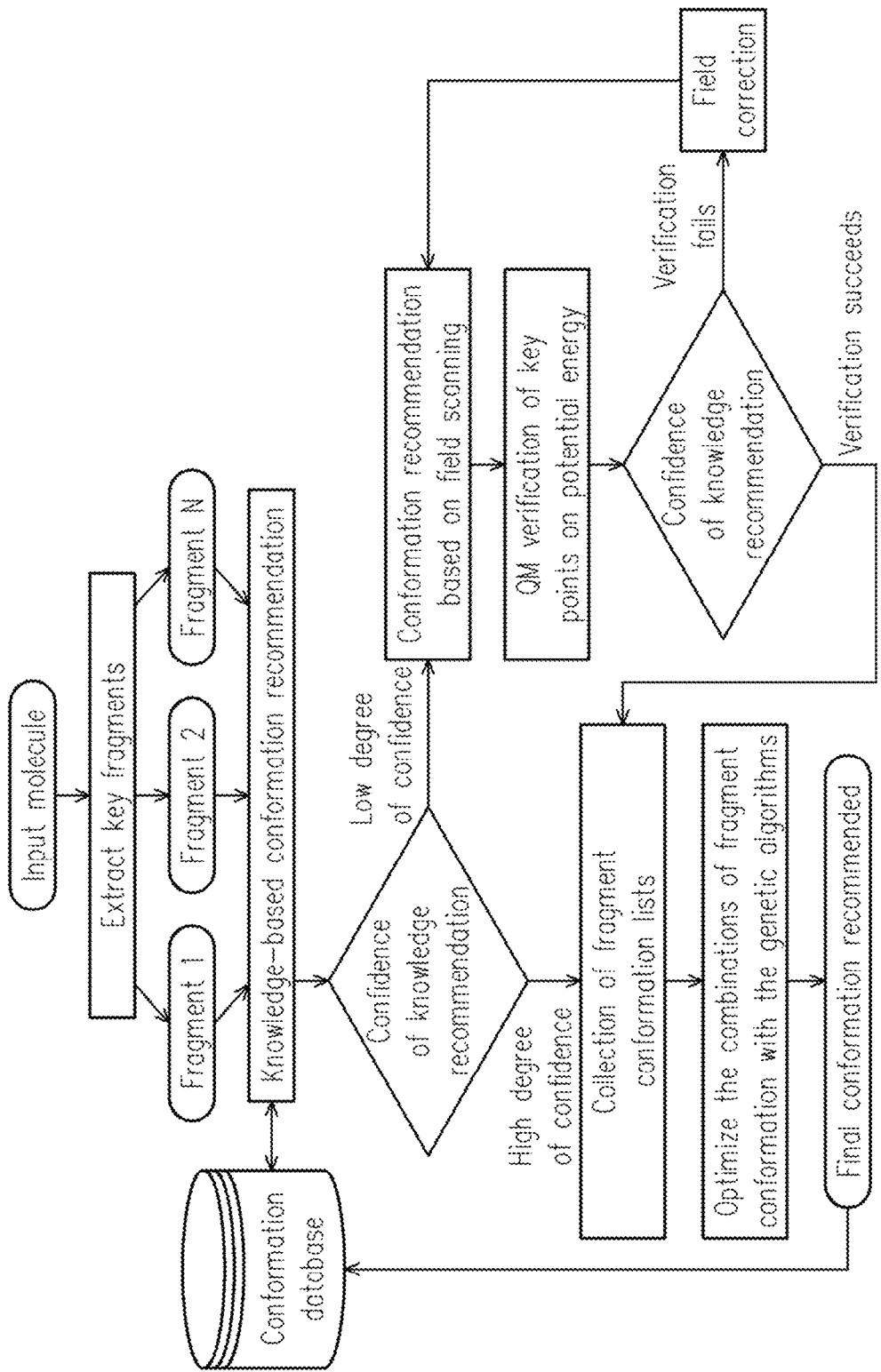
FIG. 1 is a flow diagram of the method of the invention.

FIG. 1 is a flow diagram of the method in an embodiment. As shown in FIG. 1, the method in this embodiment mainly includes the following steps.

(1) A group of fragments are extracted from an input molecule, wherein there are primarily three types of fragments: a flexible bond fragment, a ring isomerism fragment and a conformation isomerism fragment. The flexible bond fragment includes a flexible bond or two coupled flexible bonds, and an adjacent chemical group beside the flexible bond(s). Usually, whether or not two flexible bonds are in a coupled relation is determined based on a topological rule. A potential energy surface or extreme points on the flexible bond fragment are searched out by further analysis on the flexible bond fragment, so as to represent a potential energy surface of the whole molecule on this flexible bond. The ring isomerism fragment includes a non-conjugate ring or a condensed ring consisting of a plurality of rings. The conformation isomerism fragment includes one or more cis-trans sites or chiral centers, and a surrounding chemical environment. These three fragments represent three isomerism types of this molecule, and after the molecule is split into fragments, subsequent analysis is facilitated.

(2) Knowledge-based conformation recommendation is carried out. Each fragment extracted in Step (1) should be processed in this step. During actual system implementation, this step includes a conformation database which is pre-established based on experimental conformations or historical computation results. Molecular conformations including the corresponding fragments are searched out from the conformation database, and then conformation statistics of a specific flexible bond or ring isomerism, and a specified cis-trans or chiral center selected from the molecule are carried out to obtain recommended conformations and confidence coefficients of the recommended conformations. Typically, the confidence coefficients have an empirical threshold, if the confidence coefficients are greater than the empirical threshold, the credibility of the knowledge-based recommendation is considered as high, and the recommended conformations are directly used; or if the confidence coefficients are small, conformation analysis continues to be carried out in a more accurate way.

(3) Conformation recommendation based on force field scanning is carried out, wherein the following scanning strategies are mainly adopted: one-dimensional or two-dimensional equal-interval rotational scanning of flexible bonds, conformation scanning of flexible rings, and cis-trans or optical configuration scanning. Based on a molecular force field, conformations generated through the scanning strategies are rapidly optimized, and the energy of the conformations is calculated; and then reasonable conformations are screened out according to the energy.

(4) The conformations generated in step (3) are verified by QM mainly in the following two ways: positions of the extreme points are analyzed, and sampling computation is carried out on the extreme points as well as nearby points to determine by comparison whether or not QM is consistent with the positions of extreme points of the molecular force field; or, the relative energy of the recommended conformations is analyzed to verify the correlation between the QM and molecular force field computation, so that the accuracy of the force field is verified. If the verification succeeds, it indicates that the conformations recommended in Step (3) are valid; or otherwise, it is possible that the accuracy of the force field is improper, and the force field needs to be corrected next.

(5) The force field is corrected. Particularly, if a universal force field fails to accurately describe the chemical environment of the molecule, force field parameters should be improved to adapt to the molecule. Upon analysis on the corresponding fragments, QM sampling computation is additionally conducted according to the flexible bond, the ring isomerism and the conformation isomerism to serve as a training set for correcting the force field parameters, and then the force field parameters are corrected. The force field is scanned again after the force field parameters are corrected.

(6) Conformation lists of the fragments are collected. Particularly, the conformation lists separately recommended by the fragments are collected; values expressed by the conformations (including dihedral values of the flexible bonds or isomerous space parameters of the ring isomerisms, and cis-trans or chiral identifications) are extracted to be used for subsequent parameter combination and optimization.

Figure 2:
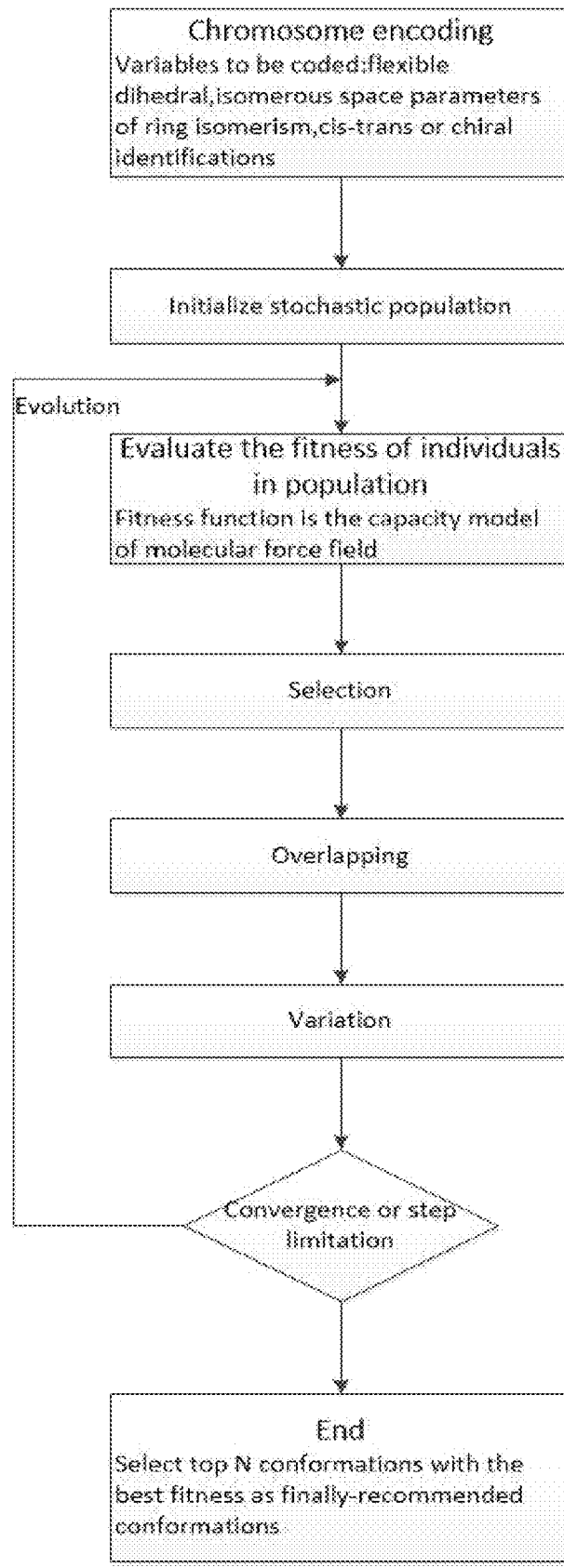
FIG. 2 is a flow diagram of the genetic algorithm of the invention.

(7) Conformation parameters of the fragments are combined and optimized through a genetic algorithm, and then a set of optimal conformations are found out through global searching. As for a large molecule including 8 flexible angles (each flexible angle has 4 extreme points), two isomerous rings (each isomerous ring has two conformations and two substitutive sites) and two chiral carbons, there may exist millions of conformation combinations ($4^8*2*2*2*2=1,048,576$) which cannot be traversed, and in this case, global searching needs to be conducted to find out a set of optimal conformations. In this application, the genetic algorithm having a simple process and a high convergence speed is adopted to execute this step. Please refer to FIG. 2 for specific details of the genetic algorithm.

Figure 3:
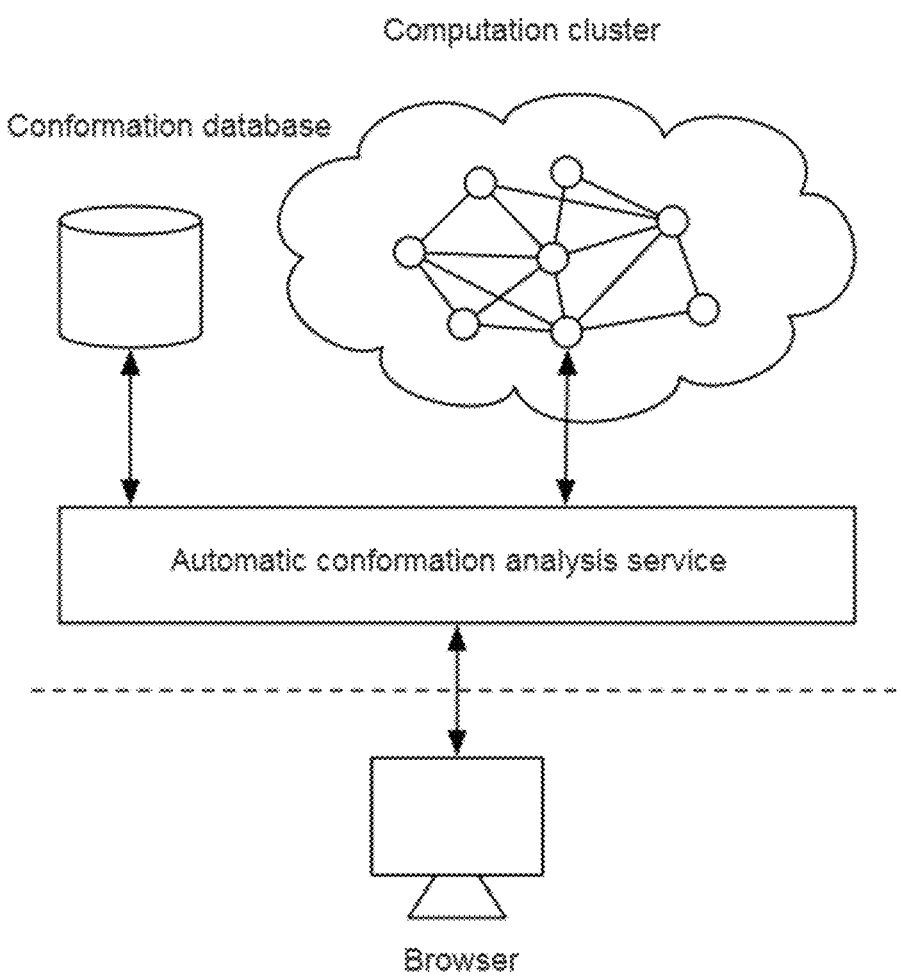
FIG. 3 is an architecture diagram of an embodiment.

Implementation of this algorithm mainly depends on the B/S architecture, as shown in FIG. 3, and users can have access to the automatic conformation analysis service via a browser and can upload 2D molecule structures to be subjected to automatic conformation analysis in a SMILES form. The automatic conformation analysis service is compiled with Python2.7 as the programming language and is deployed on a Kubernetes platform.

Users can start the whole conformation analysis process by clicking. After a molecule is uploaded, the automatic conformation analysis system initializes a query request for the conformation database which is created based on PostgreSQL 9.6 and usually includes two tables: Compound and Conformation, wherein compound information involved in the conformation database is mainly stored in Table Compound, and a set of 3D conformation information corresponding to each compound is stored in Table Conformation.

When information returned from the conformation database is insufficient, the automatic conformation analysis service submits a computation job to a computation cluster to complete subsequent computation tasks through four computation modules: a force field scanning analysis module, a QM verification module, a force field correction module and a genetic algorithm. These three modules are compiled by Python 2.7, wherein OpenMM is used as an energy computation tool in the force field part, and Psi4 is used as a computation tool in the QM part. These three computation modules adopt Docker as a creation and distribution tool to facilitate distributed task scheduling.

The automatic conformation analysis service checks the computation task in running every ten seconds and will restart the computation task three times when realizing that computation fails. This computation will be terminated after three times of restarting, and error information is fed back to users. If the computation is successfully completed, computation results will be collected and returned to users.

What is claimed is:

1. An automatic conformation analysis method for quasi-drug organic molecules, characterized in that, mainly including the following steps:
    (1) extracting a group of fragments from an input molecule, wherein there are primarily three types of fragments: a flexible bond fragment, a ring isomerism fragment, and a conformation isomerism fragment, wherein:
    the flexible bond fragment includes a flexible bond or two coupled flexible bonds, and an adjacent chemical group beside the flexible bonds, and whether or not two flexible bonds are in a coupled relation is determined based on a topological rule; a potential energy surface or extreme points on the flexible bond fragment are searched out by further analysis on the flexible bond fragment, so as to represent a potential energy surface of the whole molecule on this flexible bond;
    the ring isomerism fragment includes a non-conjugate ring or a condensed ring consisting of a plurality of rings;
    the conformation isomerism fragment includes one or more cis-trans sites or chiral centers, and a surrounding chemical environment;
    (2) canying out knowledge-based conformation recommendation, molecular conformations including the corresponding fragments extracted in step (1) are searched out from a pre-established conformation database, and then conformation statistics of a specific flexible bond or ring isomerism, and a specified cis-trans or chiral center selected from the molecule are carried out to obtain recommended conformations and confidence coefficients of the recommended conformations; the confidence coefficients comprise an empirical threshold, if the confidence coefficients are greater than the empirical threshold, a credibility of the knowledge-based recommendation is considered as high, and the recommended conformations are directly used; or if the confidence coefficients are small, the conformation analysis continues to be carried out in a more accurate way;
    (3) carrying out conformation recommendation based on force field scanning, wherein scanning strategies comprise: one-dimensional or two-dimensional equal-interval rotational scanning of flexible bonds, conformation scanning of flexible rings, and cis-trans or optical configuration scanning;
    based on a molecular force field, conformations generated through the scanning strategies are rapidly optimized, and energy of the conformations is calculated; then reasonable conformations are screened out according to the energy;

(4) verifying, by quantum mechanics (QM), the conformations generated in step (3);
if the verification succeeds, it indicates that the conformations recommended in step (3) are valid; or otherwise, the force field needs to be corrected next;

(5) correcting the force field: particularly, if a universal force field fails to accurately describe the chemical environment of the molecule, force field parameters should be improved to adapt to the molecule; upon analysis on the corresponding fragments, QM sampling computation is additionally conducted according to the flexible bond, the ring isomerism and the conformation isomerism to serve as a training set for correcting the force field parameters, and then the force field parameters are corrected; the force field is scanned again after the force field parameters are corrected;

(6) collecting conformation lists of the fragments, the conformation lists separately recommended by the fragments are collected; values expressed by the conformations (including dihedral values of the flexible bonds or isomerous space parameters of the ring isomerism, and cis-trans or chiral identifications) are extracted to be used for subsequent parameter combination and optimization; and (7) combining and optimizing confoi illation parameters of the fragments through a genetic algorithm, and finding out a set of optimal conformations through global searching.

2. The automatic conformation analysis method for quasi-drug organic molecules according to claim 1, characterized in that, wherein in step (4), the conformations are verified mainly in the following two ways:

positions of the extreme points are analyzed, and sampling computation is carried out on the extreme points as well as nearby points to determine by comparison whether or not QM is consistent with positions of extreme points of the molecular force field; or relative energy of the recommended conformations is analyzed to verify a correlation between the QM and molecular force field computation, so that the accuracy of the force field is verified.

* * * * *